United States Patent
Wang et al.

(10) Patent No.: US 12,399,167 B2
(45) Date of Patent: Aug. 26, 2025

(54) TEST METHOD FOR TOXICITY OF RAW DINOTEFURAN DRUG ON EARLY LIFE STAGE OF FISH

(71) Applicants: Zhejiang Academy of Agricultural Sciences, Hangzhou (CN); Institute of Quality Standards and Testing Technology for Agro-products of Chinese Academy of Agricultural Sciences, Beijing (CN)

(72) Inventors: Yanhua Wang, Hangzhou (CN); Guiling Yang, Hangzhou (CN); Qiang Wang, Hangzhou (CN); Chen Chen, Beijing (CN); Yongzhong Qian, Beijing (CN)

(73) Assignees: ZHEJIANG ACADEMY OF AGRICULTURAL SCIENCES, Hangzhou (CN); INSTITUTE OF QUALITY STANDARDS AND TESTING TECHNOLOGY FOR AGRO-PRODUCTS OF CHINESE ACADEMY OF AGRICULTURAL SCIENCES, Beijing (CN)

( * ) Notice: Subject to any disclaimer, the term of this patent is extended or adjusted under 35 U.S.C. 154(b) by 1547 days.

(21) Appl. No.: 16/810,514

(22) Filed: Mar. 5, 2020

(65) Prior Publication Data
US 2020/0284782 A1   Sep. 10, 2020

(30) Foreign Application Priority Data
Mar. 6, 2019   (CN) .......................... 201910169539.2

(51) Int. Cl.
*G01N 33/50*   (2006.01)
*A01N 51/00*   (2006.01)
*G06F 17/18*   (2006.01)

(52) U.S. Cl.
CPC .......... *G01N 33/5088* (2013.01); *A01N 51/00* (2013.01); *G01N 33/5014* (2013.01); *G01N 2333/4603* (2013.01); *G06F 17/18* (2013.01)

(58) Field of Classification Search
CPC ........... G01N 33/5088; G01N 33/5014; G01N 2333/4603; A01N 51/00; G06F 17/18
See application file for complete search history.

(56) References Cited

U.S. PATENT DOCUMENTS

2023/0062179 A1*   3/2023   Jiang .................. C12N 15/8213

OTHER PUBLICATIONS

Organization for Economic Co-operation and Development (OECD), Fish, Acute Toxicity Test No. 203, Jul. 17, 1992. (Year: 1992).*
International Organization for Standardization (ISO), Water quality—Determination of the acute lethal toxicity of substances to a freshwater fish [ Brachydanio rerio Hamilton-Buchanan (Teleostei, Cyprinidae)]—Part 3: Flow-through method 7346-3. 2nd edition. Jun. 15, 1996. (Year: 1996).*
Organization for Economic Co-operation and Development (OECD), Fish, Juvenile Growth Test No. 215, Jan. 21, 2000. (Year: 2000).*
Westerfield, M. (2000). The zebrafish book. A guide for the laboratory use of zebrafish (*Danio rerio*). 4th ed., Univ. of Oregon Press, Eugene. (Year: 2000).*
Bar-Ilan, Ofek, et. al., Toxicity Assessments of Multisized Gold and Silver Nanoparticles in Zebrafish Embryos. small 2009, 5, No. 16, 1897-1910. (Year: 2009).*
Lawrence, Christian, et. al. The Laboratory Zebrafish. Chapman and Hall/CRC Press. 2011. (Year: 2011).*
Liang, Jennifer, et. al., Zebrafish in the Classroom (ZFIC). How to make/use tools for handling zebrafish. http://zfic.org. 2011 (Year: 2011).*
Truong, L., et al. "Persistent adult zebrafish behavioral deficits results from acute embryonic exposure to gold nanoparticles." Comparative Biochemistry and Physiology, Part C 155 (2012) 269-274. (Year: 2012).*
Organization for Economic Co-operation and Development (OECD), Fish Embryo Acute Toxicity (FET) Test No. 236, Jul. 23, 2013. (Year: 2013).*
Organization for Economic Co-operation and Development (OECD), Fish, Early-life Stage Toxicity Test. No. 210. Jul. 26, 2013. (Year: 2013).*
Runft, D., et al., "Zebrafish as a Natural Host Model for Vibrio cholerae Colonization and Transmission." AEM 80(5) (2014) 1710-1717. (Year: 2014).*
Zhang, Q, et al., "Effects of tetracycline on developmental toxicity and molecular responses in zebrafish (*Danio rerio*) embryos." Ecotoxicology 24 (2015) 707-719 (Year: 2015).*
Li, R., et al., "Residue behaviors and dietary risk assessment of dinotefuran and its metabolites in *Oryza sativa* by a new HPLC-MS/MS method." Food Chem. 235 (2017) 188-193. (Year: 2017).*
Babić, S., et. al., "Assessment of river sediment toxicity: Combining empirical zebrafish embryotoxicity testing with in silico toxicity characterization." Science of the Total Environment 643 (2018) 435-450. (Year: 2018).*
Organization for Economic Co-operation and Development (OECD), Guidance Document on Aqueous-Phase Aquatic Toxicity Testing of Difficult Test Chemicals: Series on Testing and Assessment No. 23, 2nd edition. Feb. 8, 2019. (Year: 2019).*
EPA. Pestivide Fact Sheet. Dinotefuran Conditional Registration, Sep. 2004. (Year: 2004).*
BASF. Safety Data Sheet. Alpine D Dust Insecticide. Verison 5.0, Revision Date: May 2, 2018. (Year: 2018).*

* cited by examiner

*Primary Examiner* — Joanne Hama
*Assistant Examiner* — Amy M. Chattin
(74) *Attorney, Agent, or Firm* — Muncy, Geissler, Olds & Lowe, P.C.

(57) ABSTRACT

The present invention provides a test method for toxicity of raw dinotefuran drug on early life stage of fish. The method includes: preparing a standard diluent, preparing test drug liquids, selecting a test organism, toxicant exposure of the embryos, toxicant exposure of larvae, monitoring and controlling test conditions, observation in the test, and statistically analyzing data and drawing results.

2 Claims, No Drawings

TEST METHOD FOR TOXICITY OF RAW DINOTEFURAN DRUG ON EARLY LIFE STAGE OF FISH

CROSS-REFERENCE TO RELATED APPLICATIONS

This Non-provisional application claims priority under 35 U.S.C. § 119 (a) on Chinese Patent Application No(s). 201910169539.2 filed on Mar. 6, 2019, the entire contents of which are hereby incorporated by reference.

BACKGROUND OF THE INVENTION

Field of the Invention

The present invention belongs to the technical field of toxicity testing, and particularly relates to a method for testing toxicity of raw dinotefuran drug on fish in the early life stage.

Description of the Related Art

Dinotefuran is an anabasine type pesticide with unique chemical and biological properties. Mainly acting on insect nerves, dinotefuran can block nerves of synaptic receptors of insects. Dinotefuran is applicable to plants such as rice and vegetables, showing excellent performance on elimination of various aphids, aleyrodid, rice-leaf hoppers, and thrips. Dinotefuran has four major advantages: high efficiency, low toxicity, systemic absorption, and no cross resistance. During determination of the environment assessment of dinotefuran, the toxic effect of the dinotefuran is required to be presented. Existing test methods are complicated in procedures and fail to obtain accurate test data.

BRIEF SUMMARY OF THE INVENTION

To solve the above problems, the present invention provides a method for testing the toxicity of raw dinotefuran drug on fish in the early life stage.

The test method for toxicity of raw dinotefuran drug on early life stage of fish provided in the invention includes the following steps:
preparing a standard diluent: dissolving 11.76 g $CaCl_2 \cdot 2H_2O$ in distilled water and diluting solution to 1 L to obtain calcium chloride solution, dissolving 4.93 g $MgSO_4 \cdot 7H_2O$ in distilled water and diluting solution to 1 L to obtain magnesium sulfate solution, dissolving 2.59 g $NaHCO_3$ in distilled water and diluting solution to 1 L to obtain sodium bicarbonate solution, dissolving 0.23 g KCl in distilled water and diluting solution to 1 L to obtain potassium chloride solution, taking 25 ml of each of the four solutions, mixing, and diluting the mixed solution to 1 L with tap water which has been aerated for 24 h, wherein the standard diluent is prepared by the preceding ratio according to a required volume during testing;
preparing test drug liquids: weighing 1.786 g of raw dinotefuran drug with a purity of 98%, adding raw dinotefuran drug into a 50.0 mL volumetric flask, diluting to 50.0 mL with deionized water to obtain a mother liquid with a concentration of 35000 mg a.i./L, storing the mother liquid in a refrigerator at 4° C., adding the standard diluent into the mother liquid to prepare test drug liquids with a test concentration of 300 mg a.i./L, 150 mg a.i./L, 75.0 mg a.i./L, 37.5 mg a.i./L, 18.75 mg a.i./L and 9.375 mg a.i./L in a tolerance of +20%, respectively, and preparing a standard diluent without the raw dinotefuran drug as a control group;
selecting a test organism: wherein zebrafish is selected as the test organism, the zebrafish is AB strain, and embryos used in the test are propagated and obtained by the following methods: wherein before the test, zebrafish broodstock is reared in water at a temperature of 26±1° C., the ratio of light time to dark time is 14 h:10 h, and when it is lighted, the zebrafish broodstock is naturally illuminated in a 4.8 m×3.0 m room, plus four 40 W fluorescent lamps, and feeding lasts at least 2 weeks in an environment which is oxygenated by aeration, the zebrafish broodstock is fed once a day during pre-cultivation, and feces and food residues are removed in time
toxicant exposure of the embryos: transferring healthy zebrafish embryos laid within 4 hours with droppers into 24 well plates which serve as embryo incubation containers, adding one embryo and 2 mL of the test drug liquid into each well, setting four replicates at a time for each concentration, using a total of 4×15 embryos per concentration; then, placing the 24 well plates into an incubator at a temperature of 26±1° C., allowing incubation under a condition of 14 h light:10 h dark, and replacing the test drug liquids once every two days during this test stage;
toxicant exposure of larvae: recording the number of larvae at the end of embryo hatching, transferring the larvae into glass beakers containing 200 mL of the test drug liquid with corresponding test concentration, replacing the test drug liquids once every two days during this test stage that lasts 30 days after hatching, and feeding the larvae with yolk in the first three days and then with fairy shrimp twice a day, wherein the larvae are firstly fed on the fourth or fifth day after spawning;
monitoring and controlling test conditions: wherein temperature and dissolved oxygen of the test drug liquids where the embryos or the larvae live are measured once a week during the test, hardness and pH value of the test drug liquids are measured at the beginning and end of the test;
wherein a dissolved oxygen concentration is controlled to be 60%-80% of an air saturation value, a temperature is controlled to be 26±1° C., the pH value is controlled to be 7-8, the hardness is controlled to be 120-230 mg/L, test solubility of the test drug liquids is controlled to be within ±20% of average measurement value, a survival rate of the larvae is ensured to be no less than 70% in the control group at the end of the test; wherein the difference in water temperature among test containers is required to not exceed ±1.5° C. at the end of the test;
observation in the test: observing a hatching rate and a survival rate and recording the quantity of the larvae once a day, checking larvae's malformation, the number of malformed larvae and abnormal behaviors once a week; removing impurities and dead larvae in time, all live larvae of the control groups and test groups are anesthetized for measurement of body lengths and wet weights one by one at the end of the test, a body length of each adolescent fish is measured with a vernier caliper, and a wet weight of each adolescent fish is weighed with an electronic balance;
statistically analyzing data and drawing results: wherein according to the concentrations of the test drug liquids and the number of zebrafish hatching and deaths, using a data processing system statistical analysis software to statistically analyze the zebrafish in the early life stage to determine a unobservable effect concentration and a minimum observable effect concentration, and if concentration changes of tested substances are maintained within ±20% of the concentration of the prepared liquid during the test, formulated concentration of the prepared liquid is used in calculation.

Optionally, the test method according to claim 1, wherein the test drug liquids are replaced once every two days by the following method: newly prepared test drug liquids are added into new containers, and then live larvae are transferred into the containers with the fresh test drug liquids by droppers.

The method for testing the toxicity of raw dinotefuran drug on fish in the early life stage provided by the present invention has the following advantages: the raw materials are easily obtained, the operation is simple, and the procedure has relatively high repeatability and reliability. Compared with the existing fish test methods, the method provided by the present invention adopts zebrafish. Zebrafish in the early stages of life is usually more sensitive to contaminants, which meets the principles of reduction, substitution and optimization of current toxicological testing requirements, and has the advantages of low cost, fewer influencing factors, and higher sensitivity. By setting blank control groups at the same time, both the blank control groups and the test groups are set up with several replicates, each concentration repeats the same fish eggs, which facilitates comparison between different replicates, thus increasing reference data and improving the accuracy of data. In addition, a semi-static toxicity test is adopted to update the test drug liquid regularly, and during the test, the relevant conditions are appropriately observed and recorded by controlling the test conditions, which reduces the interference of external factors on the test and improves the accuracy of the test results.

DETAILED DESCRIPTION OF THE INVENTION

The present invention provides a method for testing the toxicity of raw dinotefuran drug on fish in the early life stage, including the following steps:

Preparation of a standard diluent: dissolving 11.76 g $CaCl_2 \cdot 2H_2O$ in distilled water and diluting the solution to 1 L to obtain calcium chloride solution, dissolving 4.93 g $MgSO_4 \cdot 7H_2O$ in distilled water and diluting the solution to 1 L to obtain magnesium sulfate solution, dissolving 2.59 g $NaHCO_3$ in distilled water and diluting the solution to 1 L to obtain sodium bicarbonate solution, dissolving 0.23 g KCl in distilled water and diluting the solution to 1 L to obtain potassium chloride solution, taking 25 ml of each of the four solutions, mixing, and diluting the mixed solution to 1 L with tap water which has been aerated for 24 h, wherein the standard diluent is prepared by the preceding ratio according to the required volume during testing.

Preparation of test drug liquids: weighing about 1.786 g of the raw dinotefuran drug with a purity of 98%, adding the raw dinotefuran drug into a 50.0 mL volumetric flask, diluting to 50.0 mL with deionized water to obtain a mother liquid with a concentration of 35000 mg a.i./L, storing the mother liquid in a refrigerator at 4° C., adding the standard diluent into the mother liquid to prepare test drug liquids with a test concentration of 300 mg a.i./L, 150 mg a.i./L, 75.0 mg a.i./L, 37.5 mg a.i./L, 18.75 mg a.i./L and 9.375 mg a.i./L in a tolerance of ±20%, respectively, and preparing a standard diluent without the raw dinotefuran drug as a blank control group. The solubility of the selected raw dinotefuran drug is 39.83 g/L in water and 57 g/L in methanol at the temperature of 20° C.

Toxicant exposure of the embryos: transferring healthy zebrafish embryos laid within 4 hours with droppers into 24 well plates which serve as embryo incubation containers, adding one embryo and 2 mL of the test drug liquid into each well, setting four replicates at a time for each concentration, using a total of 4×15 embryos per concentration; then, placing the 24 well plates into an incubator at a temperature of 26±1° C., allowing incubation under a condition of 14 h light: 10 h dark, recording the death number and the incubation time of the embryos every day, and replacing the test drug liquids once every two days during this test stage. Each concentration consumes a total of 60 embryos, and thus multiple 24 well plates are used during the test.

Selection of a test organism: zebrafish is selected as the test organism, the zebrafish is AB strain and embryos used in the test are propagated and obtained by the following methods: before the test, zebrafish broodstock is reared in water at a temperature of 26±1° C., the ratio of light time to dark time is 14 h:10 h, and when it is lighted, it should be naturally illuminated in a 4.8 m×3.0 m room, plus four 40 W fluorescent lamps, and the feeding lasts at least 2 weeks in an environment which is oxygenated by aeration, the zebrafish broodstock is fed once a day during pre-cultivation, and feces and food residues are removed in time. The zebrafish is purchased from the Institute of Hydrobiology of Chinese Academy of Science. The zebrafish has the advantages of short growth cycle, strong reproductive ability, transparent fertilized eggs, and easy observation of embryonic development, making it an important model organism in aquatic ecological toxicology research. Therefore, although the present application only carries out the toxicity test on the zebrafish in the early life stage, the method provided by the present application can be applied to the majority of fish varieties since the zebrafish is representative.

Toxicant exposure of larvae: recording the number of the larvae at the end of the embryo hatching, transferring the larvae into glass beakers containing 200 mL of the test drug liquid with the corresponding test concentration, replacing the test drug liquids once every two days during this test stage that lasts 30 days after hatching, and feeding the zebrafish larvae with yolk in the first three days and then with fairy shrimp twice a day, wherein the larvae are firstly fed on the fourth or fifth day after spawning. The feed amount is adjusted according to the actual situation so as to be able to freely ingest and avoid excess.

Monitoring and controlling test conditions: during the test, the temperature and dissolved oxygen of the test drug liquids where the embryos or larvae live are measured once a week; the hardness and pH value of the test drug liquids are measured at the beginning and end of the test; the dissolved oxygen concentration is controlled to be 60%-80% of an air saturation value (8-10 mg/L); the temperature is controlled to be 26±1° C.; the pH value is controlled to be 7-8; the hardness is controlled to be 120-230 mg/L; the test solubility of the test drug liquids is controlled to be within ±20% of the average measurement value; the survival rate of the larvae is ensured to be no less than 70% in the control group at the end of the test; and the difference in water temperature among the test containers is required to not exceed ±1.5° C. at the end of the test. The method provided by the present application has effective control over test conditions, greatly improving the accuracy of test data. During the test, if relevant test data are found to be not in the preceding scopes, then the current test is invalid, and a new test is required to be carried out again. For example, if the survival rate of the adolescent fish in the control group is lower than 70% at the end of the test, the current test is invalid, and a new test is required to be carried out again.

Observation in the test: observing the hatching rate and survival rate and recording the quantity of the larvae once a day; checking the larvae's malformation, the number of malformed larvae and abnormal behaviors once a week; removing impurities and dead larvae in beakers in a timely manner; all live larvae of the control groups and the concentration test groups are anesthetized with MS-222 for measurement of the body lengths and wet weights one by one at the end of the test, wherein the body length of each adolescent fish is measured with a vernier caliper, and the wet weight of each adolescent fish is weighed with an electronic balance. The reciprocal sensibility of the electronic balance is 0.00001 g, and the moisture on the body surface of each fish needs to be removed when the wet weight is weighed.

Statistically analyzing the data and drawing the results: according to the concentrations of the test drug liquids and the number of zebrafish hatching and deaths, using a data processing system (DPS) statistical analysis software to statistically analyze the zebrafish in the early life stage to determine the unobservable effect concentration and the minimum observable effect concentration, and if the concentration changes of the tested substances are maintained within ±20% of the concentration of the prepared liquid during the test, the formulated concentration of the prepared liquid is used in determination. DPS statistical analysis software is the existing software and therefore is not described in detail here. Any other software that can implement the statistical analysis function is also available.

In this embodiment, apparatus and equipment include an AB135-S electronic balance (used for weighing the raw drug and the reagents for preparing the standard diluent), a BSA 223S electronic balance (used for weighing fish), a Sanyo MLR-350HT incubator, a CD-6OSX digital vernier caliper, an SX-620 pH pen, a HACH HQ30d dissolved oxygen analyzer, a HANNA HI96735 water hardness meter, a KQ2200 ultrasonic cleaner, a rotary evaporator, pipette, 24 well plates, 500 mL beakers, and 1000 mL volumetric flasks.

Optionally, the test drug liquids are replaced once every two days in the following way: newly prepared test drug liquids are added into new containers, and then the live larvae are transferred into the containers with the fresh test drug liquid by using droppers. Optionally, the droppers are plastic droppers. The used plastic droppers are disposable, low in price and convenient in use, and avoid interference from external factors.

The present application involves the measurement of the numerical values of the temperature, hardness, dissolved oxygen and pH value of the test drug liquid, and then the number of embryos hatched each day, the number of deaths, the starting time of hatching and the total hatching time and the number of larvae hatched each day are counted. Specifically, during the test, the dissolved oxygen range was 8.19-9.92 mg/L, the temperature was 25.3-26.8° C., the pH was between 7.59-7.96, and the hardness was 158-209 mg/L, and all are within the allowable range of the test. During the exposure stage of the test, no obvious toxic symptoms were observed except malformation of several fishes before death in the test groups. The quantity and body lengths of live fish at the end of the test can be seen in the attached Table 1, and the weights of the live fish can be seen in Table 2. The test results show that: at the end of the test, all larvae in the treatment groups with the test concentrations of 300 and 150 mg a.i./L died; the death rate of the larvae is 55.0% in the treatment groups with the test concentration of 75.0 mg a.i./L, 46.67% in the treatment groups with the test concentration of 37.5 mg a.i./L, and 41.67% in the treatment groups with the test concentration of 18.75 mg a.i./L, which is obviously different from the 25.0% death rate in the control groups; the body lengths of the larvae in the treatment groups of 75.0 mg a.i./L and 37.5 mg a.i./L concentrations are obviously different from the body length of the control groups; the weights of the larvae in the test groups of 75.0, 37.5. 18.75 and 9.375 mg a.i./L concentrations are obviously different from those in the control groups; at the end of the test, the unobservable effect concentration on the body lengths of the larvae is 18.75 mg a.i./L, and the minimum observable effect concentration is 37.5 mg a.i./L; and the minimum observable effect concentration on the weights of the larvae is 9.375 mg a.i./L at the end of the test. The minimum observable effect concentration refers to the minimum concentration where the dinotefuran generates a negative influence on the zebrafish, and the unobservable effect concentration refers to the maximum concentration where the toxic effect of dinotefuran on the zebrafish is not observed and that is obviously statistically different from the blank control groups. Therefore, the toxic data of dinotefuran on the zebrafish in the early life stage obtained by the present application provides a more accurate scientific basis for establishing the water quality criteria for dinotefuran.

TABLE 1

Length measurement and death rate of larvae

| Concentration of the prepared liquid mg a.i./L | Repeating group | Length of each live fish (mm) | | | | | | | | | | |
|---|---|---|---|---|---|---|---|---|---|---|---|---|
| | | 1 | 2 | 3 | 4 | 5 | 6 | 7 | 8 | 9 | 10 | 11 |
| 300 | 1 | NA | NA | NA | NA | NA | NA | NA | NA | NA | NA | NA |
| | 2 | NA | NA | NA | NA | NA | NA | NA | NA | NA | NA | NA |
| | 3 | NA | NA | NA | NA | NA | NA | NA | NA | NA | NA | NA |
| | 4 | NA | NA | NA | NA | NA | NA | NA | NA | NA | NA | NA |
| 150 | 1 | NA | NA | NA | NA | NA | NA | NA | NA | NA | NA | NA |
| | 2 | NA | NA | NA | NA | NA | NA | NA | NA | NA | NA | NA |
| | 3 | NA | NA | NA | NA | NA | NA | NA | NA | NA | NA | NA |
| | 4 | NA | NA | NA | NA | NA | NA | NA | NA | NA | NA | NA |
| 75.0 | 1 | 11.57 | 14.55 | 13.25 | 13.55 | 8.55 | 14.31 | 13.59 | 14.31 | NA | NA | NA |
| | 2 | 14.55 | 13.51 | 14.58 | 11.24 | 11.54 | 11.25 | 11.41 | NA | NA | NA | NA |
| | 3 | 13.16 | 14.42 | 11.66 | 13.64 | 11.21 | 12.46 | 13.28 | NA | NA | NA | NA |
| | 4 | 11.26 | 11.55 | 14.36 | 13.22 | 14.63 | NA | NA | NA | NA | NA | NA |

TABLE 1-continued

Length measurement and death rate of larvae

| | | | | | | | | | | | | |
|---|---|---|---|---|---|---|---|---|---|---|---|---|
| 37.5 | 1 | 11.56 | 14.25 | 13.86 | 12.44 | 11.65 | 13.63 | 14.56 | 14.69 | NA | NA | NA |
| | 2 | 14.88 | 11.48 | 12.54 | 15.66 | 14.51 | 14.68 | 11.44 | NA | NA | NA | NA |
| | 3 | 14.66 | 15.25 | 11.63 | 11.46 | 15.52 | 12.54 | 13.88 | 14.63 | 13.54 | NA | NA |
| | 4 | 12.88 | 13.62 | 14.23 | 13.62 | 8.54 | 14.66 | 14.56 | 15.66 | NA | NA | NA |
| 18.75 | 1 | 15.56 | 14.25 | 14.63 | 16.34 | 15.66 | 15.24 | 16.54 | 15.88 | NA | NA | NA |
| | 2 | 16.66 | 16.22 | 13.28 | 15.26 | 16.65 | 16.66 | 15.64 | 15.88 | 14.85 | 15.37 | NA |
| | 3 | 16.53 | 16.64 | 16.18 | 16.31 | 16.66 | 15.64 | 16.54 | 15.55 | 16.64 | NA | NA |
| | 4 | 16.66 | 15.61 | 16.65 | 16.66 | 15.11 | 16.31 | 13.62 | 16.31 | NA | NA | NA |
| 9.375 | 1 | 15.26 | 15.86 | 16.25 | 13.55 | 16.46 | 17.41 | 16.31 | 14.25 | 16.26 | 16.64 | 15.61 |
| | 2 | 15.85 | 15.41 | 16.42 | 16.26 | 16.46 | 17.64 | 16.44 | 13.62 | 15.16 | 13.62 | 14.64 |
| | 3 | 16.14 | 16.54 | 14.68 | 16.41 | 16.36 | 16.32 | 16.41 | 16.14 | 14.24 | 16.15 | 16.58 |
| | 4 | 16.66 | 16.44 | 16.28 | 14.68 | 16.54 | 16.22 | 16.38 | 15.64 | 16.18 | NA | NA |
| 0 | 1 | 16.28 | 16.36 | 15.25 | 15.66 | 15.21 | 13.81 | 16.21 | 16.52 | 16.22 | 16.46 | 16.32 |
| | 2 | 16.65 | 16.56 | 15.53 | 16.11 | 16.23 | 16.58 | 16.58 | 16.46 | 14.82 | 16.65 | 16.52 |
| | 3 | 16.41 | 16.21 | 16.66 | 16.41 | 16.38 | 15.62 | 16.36 | 16.24 | 16.41 | 16.14 | 16.26 |
| | 4 | 16.41 | 16.41 | 16.62 | 15.42 | 16.14 | 16.61 | 16.14 | 13.26 | 16.66 | 16.22 | 16.22 |

| Concentration of the prepared liquid mg a.i./L | Repeating group | Length of each live fish (mm) | | | | AL (mm) | NH (Piece) | AM (%) |
|---|---|---|---|---|---|---|---|---|
| | | 12 | 13 | 14 | 15 | | | |
| 300 | 1 | NA | NA | NA | NA | NA | NA | NA |
| | 2 | NA | NA | NA | NA | | | |
| | 3 | NA | NA | NA | NA | | | |
| | 4 | NA | NA | NA | NA | | | |
| 150 | 1 | NA | NA | NA | NA | NA | NA | NA |
| | 2 | NA | NA | NA | NA | | | |
| | 3 | NA | NA | NA | NA | | | |
| | 4 | NA | NA | NA | NA | | | |
| 75.0 | 1 | NA | NA | NA | NA | 12.83 ± 1.53 b | 27 | 55.0 b |
| | 2 | NA | NA | NA | NA | | | |
| | 3 | NA | NA | NA | NA | | | |
| | 4 | NA | NA | NA | NA | | | |
| 37.5 | 1 | NA | NA | NA | NA | 13.52 ± 1.61 b | 32 | 46.67 b |
| | 2 | NA | NA | NA | NA | | | |
| | 3 | NA | NA | NA | NA | | | |
| | 4 | NA | NA | NA | NA | | | |
| 18.75 | 1 | NA | NA | NA | NA | 15.83 ± 0.88 a | 35 | 41.67 b |
| | 2 | NA | NA | NA | NA | | | |
| | 3 | NA | NA | NA | NA | | | |
| | 4 | NA | NA | NA | NA | | | |
| 9.375 | 1 | NA | NA | NA | NA | 15.86 ± 0.95 a | 44 | 26.67 a |
| | 2 | 16.24 | 15.24 | NA | NA | | | |
| | 3 | NA | NA | NA | NA | | | |
| | 4 | NA | NA | NA | NA | | | |
| 0 | 1 | 16.65 | 15.13 | NA | NA | 16.08 ± 0.72 a | 45 | 25.0 a |
| | 2 | NA | NA | NA | NA | | | |
| | 3 | NA | NA | NA | NA | | | |
| | 4 | NA | NA | NA | NA | | | |

Notes:
AL: Average length of live fish
NH: Number of health fish
AM: Accumulative mortality
NA represents "non-applicable"

TABLE 2

Records on larvae weighing

| Concentration of the prepared liquid mg/L | Repeating group | Quantity of test objects | Weight of each live fish (mg) | | | | | | | |
|---|---|---|---|---|---|---|---|---|---|---|
| | | | 1 | 2 | 3 | 4 | 5 | 6 | 7 | 8 |
| 300 | 1 | 15 | NA | NA | NA | NA | NA | NA | NA | NA |
| | 2 | 15 | NA | NA | NA | NA | NA | NA | NA | NA |
| | 3 | 15 | NA | NA | NA | NA | NA | NA | NA | NA |
| | 4 | 15 | NA | NA | NA | NA | NA | NA | NA | NA |

TABLE 2-continued

Records on larvae weighing

| Concentration of the prepared liquid mg/L | Repeating group | | Weight of each live fish (mg) | | | | | | | |
|---|---|---|---|---|---|---|---|---|---|---|
| | | | 1 | 2 | 3 | 4 | 5 | 6 | 7 | 8 |
| 150 | 1 | 15 | NA | NA | NA | NA | NA | NA | NA | NA |
| | 2 | 15 | NA | NA | NA | NA | NA | NA | NA | NA |
| | 3 | 15 | NA | NA | NA | NA | NA | NA | NA | NA |
| | 4 | 15 | NA | NA | NA | NA | NA | NA | NA | NA |
| 75.0 | 1 | 15 | 12.85 | 13.81 | 17.43 | 13.17 | 13.55 | 14.17 | 11.76 | 12.08 |
| | 2 | 15 | 17.77 | 15.53 | 7.55 | 15.55 | 14.77 | 13.55 | 15.5 | NA |
| | 3 | 15 | 15.21 | 7.37 | 17.45 | 13.2 | 8.51 | 10.38 | 11.16 | NA |
| | 4 | 15 | 15.87 | 15.05 | 14.57 | 13.03 | 7.58 | NA | NA | NA |
| 37.5 | 1 | 15 | 13.01 | 15.42 | 14.75 | 12.84 | 15.57 | 13.5 | 7.74 | 13.64 |
| | 2 | 15 | 13.41 | 15.35 | 15.54 | 14.57 | 12.48 | 8.51 | 12.7 | NA |
| | 3 | 15 | 12.73 | 15.4 | 17.77 | 14.85 | 13.52 | 15.77 | 12.57 | 15.5 |
| | 4 | 15 | 13.84 | 15.1 | 14.82 | 14.77 | 15.07 | 13.18 | 12.85 | 13.5 |
| 18.75 | 1 | 15 | 14.83 | 13.84 | 12.47 | 14.77 | 13.78 | 15.55 | 14.7 | 13.8 |
| | 2 | 15 | 13.75 | 15.5 | 13.54 | 13.37 | 14.17 | 12.07 | 15.57 | 15.22 |
| | 3 | 15 | 14.51 | 14.77 | 12.13 | 14.77 | 7.54 | 13.14 | 15.8 | 15.3 |
| | 4 | 15 | 14.43 | 12.3 | 14.14 | 13.78 | 15.57 | 15.55 | 17.55 | 15.8 |
| 9.375 | 1 | 15 | 14.77 | 17.85 | 15.85 | 15.77 | 17.75 | 15.01 | 15.07 | 17.18 |
| | 2 | 15 | 15.21 | 15.42 | 15.57 | 17.5 | 15.75 | 17.27 | 20.85 | 20.5 |
| | 3 | 15 | 13.42 | 17.77 | 15.7 | 15.47 | 15.27 | 18.2 | 20.77 | 18.2 |
| | 4 | 15 | 18.77 | 15.58 | 13.47 | 15.15 | 18.04 | 15.01 | 17.08 | 18.4 |
| 0 | 1 | 15 | 18.2 | 20.77 | 17.54 | 17.75 | 18.2 | 18.54 | 20.87 | 21.05 |

| Concentration of the prepared liquid mg/L | Repeating group | Weight of each live fish (mg) | | | | | | | Average weight of Live fish (mg) |
|---|---|---|---|---|---|---|---|---|---|
| | | 9 | 10 | 11 | 12 | 13 | 14 | 15 | |
| 300 | 1 | NA | NA | NA | NA | NA | NA | NA | NA |
| | 2 | NA | NA | NA | NA | NA | NA | NA | |
| | 3 | NA | NA | NA | NA | NA | NA | NA | |
| | 4 | NA | NA | NA | NA | NA | NA | NA | |
| 150 | 1 | NA | NA | NA | NA | NA | NA | NA | NA |
| | 2 | NA | NA | NA | NA | NA | NA | NA | |
| | 3 | NA | NA | NA | NA | NA | NA | NA | |
| | 4 | NA | NA | NA | NA | NA | NA | NA | |
| 75.0 | 1 | NA | NA | NA | NA | NA | NA | NA | 13.29 ± 2.96 c |
| | 2 | NA | NA | NA | NA | NA | NA | NA | |
| | 3 | NA | NA | NA | NA | NA | NA | NA | |
| | 4 | NA | NA | NA | NA | NA | NA | NA | |
| 37.5 | 1 | NA | NA | NA | NA | NA | NA | NA | 13.89 ± 1.96 c |
| | 2 | NA | NA | NA | NA | NA | NA | NA | |
| | 3 | 14.77 | NA | NA | NA | NA | NA | NA | |
| | 4 | NA | NA | NA | NA | NA | NA | NA | |
| 18.75 | 1 | NA | NA | NA | NA | NA | NA | NA | 14.21 ± 1.68 c |
| | 2 | 15.3 | 13.62 | NA | NA | NA | NA | NA | |
| | 3 | 15.07 | NA | NA | NA | NA | NA | NA | |
| | 4 | NA | NA | NA | NA | NA | NA | NA | |
| 9.375 | 1 | 15.5 | 17.18 | 15.37 | NA | NA | NA | NA | 16.53 ± 2.18 b |
| | 2 | 17.5 | 17.75 | 17.5 | 8.75 | 17.5 | NA | NA | |
| | 3 | 15.21 | 13.77 | 18.2 | NA | NA | NA | NA | |
| | 4 | 19.64 | NA | NA | NA | NA | NA | NA | |
| 0 | 1 | 17.08 | 17.55 | 20.57 | 17.55 | 20.37 | NA | NA | 18.43 ± 1.60 a |

What is claimed is:

1. A test method for toxicity of raw dinotefuran drug on early life stage of fish, comprising the following steps:

preparing a standard diluent: dissolving 11.76 g $CaCl_2 \cdot 2H_2O$ in distilled water and diluting solution to 1 L to obtain calcium chloride solution, dissolving 4.93 g $MgSO_4 \cdot 7H_2O$ in distilled water and diluting solution to 1 L to obtain magnesium sulfate solution, dissolving 2.59 g $NaHCO_3$ in distilled water and diluting solution to 1 L to obtain sodium bicarbonate solution, dissolving 0.23 g KCl in distilled water and diluting solution to 1 L to obtain potassium chloride solution, taking 25 ml of each of the four solutions, mixing, and diluting the mixed solution to 1 L with tap water which has been aerated for 24 h, wherein the standard diluent is prepared by the preceding ratio according to a required volume during testing;

preparing test drug liquids: weighing 1.786 g of raw dinotefuran drug with a purity of 98%, adding raw dinotefuran drug into a 50.0 mL volumetric flask, diluting to 50.0 mL with deionized water to obtain a mother liquid with a concentration of 35000 mg a.i./L, storing the mother liquid in a refrigerator at 4° C., adding the standard diluent into the mother liquid to prepare test drug liquids with a test concentration of 300 mg a.i./L, 150 mg a.i./L, 75.0 mg a.i./L, 37.5 mg a.i./L, 18.75 mg a.i./L and 9.375 mg a.i./L in a tolerance of ±20%, respectively, and preparing a standard diluent without the raw dinotefuran drug as a control group;

selecting a test organism: wherein zebrafish is selected as the test organism, the zebrafish is AB strain, and embryos used in the test are propagated and obtained by the following methods: wherein before the test, zebrafish broodstock is reared in water at a temperature of 26±1° C., the ratio of light time to dark time is 14 h:10 h, and when it is lighted, the zebrafish broodstock is naturally illuminated in a 4.8 m×3.0 m room, plus four 40 W fluorescent lamps, and feeding lasts at least 2 weeks in an environment which is oxygenated by aeration, the zebrafish broodstock is fed once a day during pre-cultivation, and feces and food residues are removed in time toxicant exposure of the embryos: transferring healthy zebrafish embryos laid within 4 hours with droppers into 24 well plates which serve as embryo incubation containers, adding one embryo and 2 mL of the test drug liquid into each well, setting four replicates at a time for each concentration, using a total of 4×15 embryos per concentration; then, placing the 24 well plates into an incubator at a temperature of 26±1° C., allowing incubation under a condition of 14 h light: 10 h dark, and replacing the test drug liquids once every two days during this test stage;

toxicant exposure of adolescent fish: recording the number of adolescent fish at the end of embryo hatching, transferring the adolescent fish into glass beakers containing 200 mL of the test drug liquid with corresponding test concentration, replacing the test drug liquids once every two days during this test stage that lasts 30 days after hatching, and feeding the adolescent fish with yolk in the first three days and then with fairy shrimp twice a day, wherein the adolescent fish are firstly fed on the fourth or fifth day after spawning;

monitoring and controlling test conditions: wherein temperature and dissolved oxygen of the test drug liquids where the embryos or the adolescent fish live are measured once a week during the test, hardness and pH value of the test drug liquids are measured at the beginning and end of the test; wherein a dissolved oxygen concentration is controlled to be 60%-80% of an air saturation value, a temperature is controlled to be 26±1° C., the pH value is controlled to be 7-8, the hardness is controlled to be 120-230 mg/L, test solubility of the test drug liquids is controlled to be within ±20% of average measurement value, a survival rate of the adolescent fish is ensured to be no less than 70% in the control group at the end of the test; wherein the difference in water temperature among test containers is required to not exceed ±1.5° C. at the end of the test;

observation in the test: observing a hatching rate and a survival rate and recording the quantity of the adolescent fish once a day, checking adolescent fish's malformation, the number of malformed adolescent fish and abnormal behaviors once a week; removing impurities and dead adolescent fish in time, all live adolescent fish of the control groups and test groups are anesthetized for measurement of body lengths and wet weights one by one at the end of the test, a body length of each of the adolescent fish is measured with a vernier caliper, and a wet weight of each of the adolescent fish is weighed with an electronic balance;

statistically analyzing data and drawing results: wherein according to the concentrations of the test drug liquids and the number of zebrafish hatching and deaths, using a data processing system statistical analysis software to statistically analyze the zebrafish in the early life stage to determine a unobservable effect concentration and a minimum observable effect concentration, and if concentration changes of tested substances are maintained within ±20% of the concentration of the prepared liquid during the test, formulated concentration of the prepared liquid is used in calculation.

2. The test method according to claim 1, wherein the test drug liquids are replaced once every two days by the following method: newly prepared test drug liquids are added into new containers, and then live adolescent fish are transferred into the containers with the fresh test drug liquids by droppers.

\* \* \* \* \*